(12) United States Patent
Bennett et al.

(10) Patent No.: US 11,389,369 B2
(45) Date of Patent: Jul. 19, 2022

(54) APPARATUS AND METHOD OF TREATING PREMATURE EJACULATION

(71) Applicant: Morari, LLC, Maple Grove, MN (US)

(72) Inventors: Jeffrey Bennett, Maple Grove, MN (US); William Rissmann, Deephaven, MN (US)

( * ) Notice: Subject to any disclaimer, the term of this patent is extended or adjusted under 35 U.S.C. 154(b) by 164 days.

(21) Appl. No.: 16/618,099

(22) PCT Filed: Jun. 13, 2018

(86) PCT No.: PCT/US2018/037222
§ 371 (c)(1),
(2) Date: Nov. 27, 2019

(87) PCT Pub. No.: WO2018/231911
PCT Pub. Date: Dec. 20, 2018

(65) Prior Publication Data
US 2021/0137777 A1    May 13, 2021

Related U.S. Application Data

(60) Provisional application No. 62/520,122, filed on Jun. 15, 2017.

(51) Int. Cl.
*A61H 19/00* (2006.01)
*A61H 23/02* (2006.01)

(52) U.S. Cl.
CPC ............. *A61H 19/32* (2013.01); *A61H 19/50* (2013.01); *A61H 23/0245* (2013.01); *A61H 2201/1207* (2013.01); *A61H 2201/165* (2013.01); *A61H 2201/1654* (2013.01); *A61H 2201/1685* (2013.01); *A61H 2201/5048* (2013.01); *A61H 2201/5058* (2013.01); *A61H 2201/5097* (2013.01)

(58) Field of Classification Search
CPC ........ A61H 19/00; A61H 19/32; A61H 19/50; A61H 23/0245
See application file for complete search history.

(56) References Cited

U.S. PATENT DOCUMENTS

| | | | |
|---|---|---|---|
| 2002/0055702 A1* | 5/2002 | Atala | A61M 37/0092 604/20 |
| 2005/0283044 A1* | 12/2005 | Chang | A61F 5/41 600/38 |
| 2008/0065187 A1* | 3/2008 | Squicciarini | A61F 2/26 607/143 |
| 2011/0288370 A1* | 11/2011 | Orten | A61H 19/32 600/38 |
| 2015/0088112 A1* | 3/2015 | Barman | A61B 18/1492 606/21 |
| 2015/0141880 A1* | 5/2015 | Ehrenreich | A61H 19/30 601/47 |
| 2017/0135895 A1* | 5/2017 | Jafri | A61H 23/02 |
| 2018/0353372 A1* | 12/2018 | Liyanage | A61B 5/4393 |

* cited by examiner

*Primary Examiner* — John P Lacyk
(74) *Attorney, Agent, or Firm* — Skaar Ulbrich Macari, P.A.

(57) ABSTRACT

A neuromodulation such as ultrasound therapy having a cuff and transducer to removably position on a penis of a patient in order to treat premature ejaculation. The transducer stimulates a dorsal nerve of the penis in order to stimulate or inhibit the nerve pathway between the penis and the brain in order to delay ejaculation until the user or their partner desires to have an ejaculation occur.

20 Claims, 4 Drawing Sheets

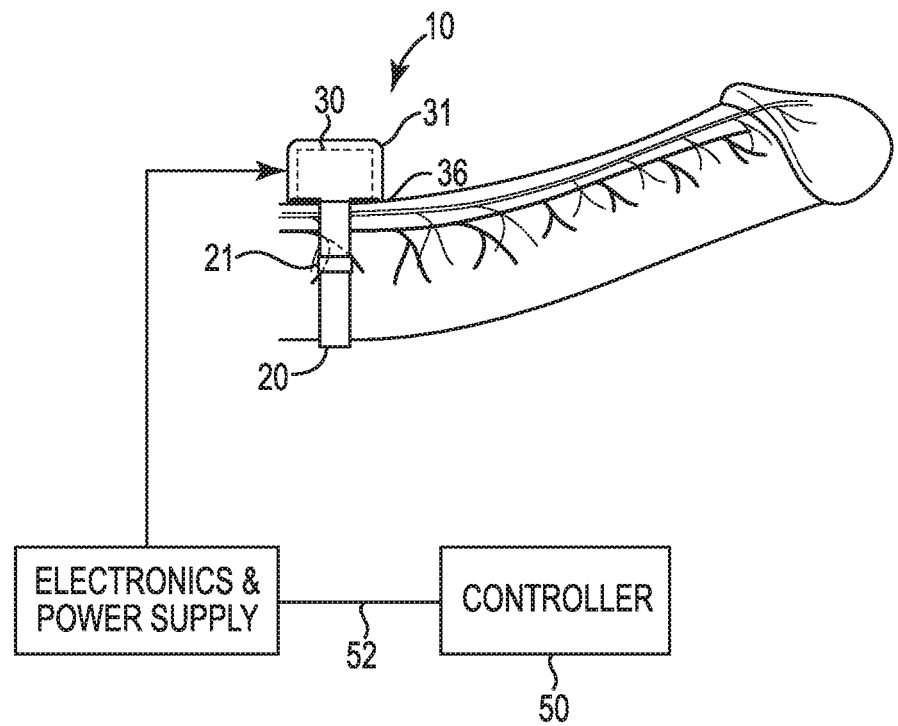
FIG. 1
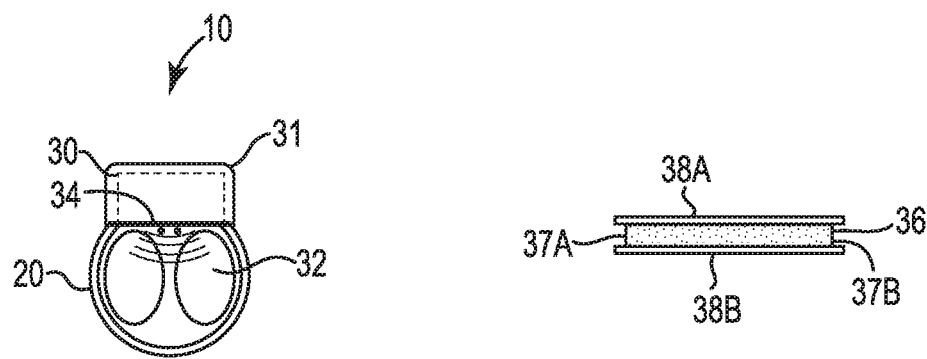
FIG. 2
FIG. 3

APPARATUS AND METHOD OF TREATING PREMATURE EJACULATION

PRIORITY

This application claims priority to and the benefit of PCT Patent Application No. PCT/US2018/037222 filed on Jun. 13, 2018 and which claims the benefit of U.S. Provisional Application No. 62/520,122, filed on Jun. 15, 2017, both of which are hereby incorporated herein by reference in its entirety.

FIELD

The present invention relates generally to the treatment of premature ejaculation in a male and, more particularly, to an apparatus and method using neuromodulation techniques to include ultrasound waves as a means of stimulating or inhibiting the dorsal nerve of the penis or pudendal nerve of a patient, thereby preventing premature ejaculation or prolonging ejaculation.

BACKGROUND

A number of devices and methods are available for enabling those with premature ejaculation to delay an ejaculatory event. These devices and method are generally either applied to the surface of the penis, in the form of a pharmacological cream, or are implanted within or proximate to the penis in order to deliver an electrical pulse to a nerve of the penis.

Generally speaking, the methods that are available, or which have been described, include the use of various constriction devices. These devices, like the one described in U.S. Pat. No. 5,921,914 have been used for centuries and are typically applied around a base of a penis to constrict it. The constriction causes the penis to stay erect and is supposed to prevent an ejaculatory event. The problem with these constriction devices is that blood is prevented from flowing out of the penis. This permits a blood pooling effect that can causes the temperature of the penis to drop causing it to feel cold. This can be unpleasant for the person suffering from premature ejaculation and their sexual partner.

In order to overcome the shortcomings of the constriction devices, various compounds were developed to treat premature ejaculation. These compounds have traditionally taken the form of topical anesthetic compounds. The problem with topical compounds is that they are typically applied shortly before a sexual encounter. The application of the topical compound in proximity to a sexual encounter has often resulted in a transfer of the topical compound to a sexual partner. As a result, the partner of an individual suffering from premature ejaculation can be exposed to the compound thereby desensitizing their sexual organs and delaying or negatively impacting their experience. As such, topical compounds have failed to provide an effective solution to individuals suffering from premature ejaculation.

In order to counter the problems associated with topical compounds, patients have been prescribed antidepressants as a form of treatment. The use of antidepressants has been widely disclosed, including in U.S. Pat. Nos. 4,507,323; 4,940,731; 5,151,448; and 5,276,042. These drugs have had some success; however, their efficacy tends to decrease over time and they are plagued with serious side effects that causes patient to stop using the drugs.

When topical compounds and drugs failed to provide an adequate solution, medical device companies developed various electrical stimulation devices that stimulate the nerves of the penis in an attempt to prevent premature ejaculation. For instance, in U.S. Pat. No. 7,328,069 to Gerber, Medtronic has developed a device that is implantable into an abdomen of a patient with leads extending into a patient's pelvic cavity to stimulate the pudendal nerve. The problem of implantable devices is that they carry the shortcomings of all the complications associated with surgery, including but not limited infection. Others developed electrical stimulation devices that did not have to be implanted but would rather be placed over the penis. These devices, like the one described in U.S. Pat. No. 9,017,244 to Chiu, used cuffs or condom shaped devices that would deliver electrical stimulation to the penis. Unfortunately, these devices created electrical stimulations or shocks that some patients found unpleasant.

In all of the devices available or described a need has remained for an improved means for treating premature ejaculation or prolonging ejaculation in non-premature ejaculation men. It is thus apparent that a device and method of treating premature ejaculation that doesn't negatively impact the experience of both the sufferer and partner, nor requires implantation would be very desirable.

SUMMARY

The present invention discloses devices, systems, and methods for treatment of a sexual dysfunction such as premature ejaculation or in general, prolonged ejaculation. Premature ejaculation is a condition that is currently impacting up to 30% of men worldwide. The invention is intended to transdermally stimulate or inhibit the dorsal nerve of the penis or pudendal nerve, thereby inhibiting or stimulating the nerve pathway between the penis and the brain in order to delay ejaculation until the male or female desires to have an ejaculation occur.

In one example embodiment of the invention a cuff or ring is removably secured to a portion of the penis. The cuff may be secured to at the base of the penis to deliver the treatment. The cuff may include a mechanism incorporated therein or thereon, such as a wave producing mechanism generated by an ultrasound crystal, to create waves that interfere with various nerves of the penis. The waves are transmitted at a frequency that interferes with the signal pathway thus delaying an ejaculatory event. In another example embodiment of the invention, the cuff may contain other elements (electrical, mechanical, chemical or magnetic) that when activated would also interfere with nerve signals from the penis to delay ejaculation.

The present invention may also include a wired or wireless controller that controls the one or more elements within or on the cuff or ring. The controller would be activated via a dedicated device or a smart phone, watch or similar device that someone would wear or hold or be activated by voice commands. Anyone having control of the device would be able to activate or deactivate the elements within or on the cuff or ring by control of the controller. When deactivated, the elements within or on the cuff or ring would cease interfering with nerve signals transmitted between the penis and the brain. When activated, however, they would interfere with the nerve signals being propagated along the nerve. The level of nerve signal interference is controlled by the person holding or wearing the controller so that the timing of desired ejaculation could be controlled by either party. While the intent of the invention is to create and external device, the same invention elements may apply to a minimally invasive implantable device to prolong ejaculation.

The above summary is not intended to limit the scope of the invention, or describe each embodiment, aspect, implementation, feature or advantage of the invention. The detailed technology and preferred embodiments for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIG. 1 is a perspective view of the premature ejaculation treatment system according to an example embodiment.

FIG. 2 is an end view of the premature ejaculation treatment system according to an example embodiment of the invention.

FIG. 3 is a cross sectional view of a coupling member used with a transducer according to an example embodiment.

Figure 4:
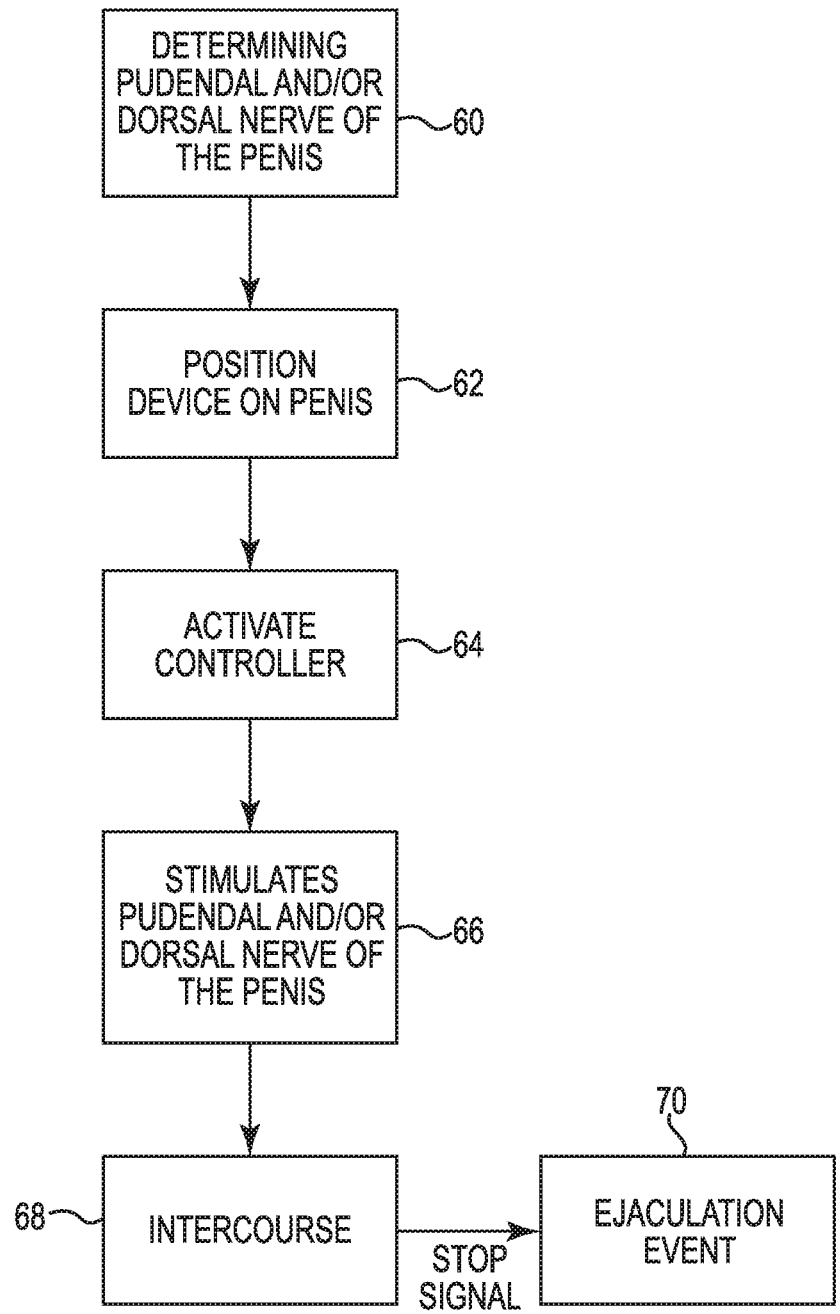
FIG. 4 is a schematic diagram of the method of treating premature ejaculation according to an example embodiment of the invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

Dimensions and relative proportions of components are merely example embodiments and can be varied unless specifically limited in a given claim. Thus, the dimensions can be varied without departing from the scope of the invention.

The present invention illustrates devices, systems, and methods for treating sexual dysfunctions such as premature ejaculation. While the invention is particularly advantageous for patients suffering from a sexual dysfunction such as premature ejaculation, it may also be used by anyone that desires to delay or alter sexual emissions. The present invention may also be used as a means of desensitizing a sexual organ for the purpose of altering sexual activity or emissions. The present invention may have application in humans as well as veterinary applications.

In one example embodiment of the invention, as illustrated in FIGS. 1-3 and 5-7, a device, method or ejaculate emission delay system 10 is shown for controlling the premature emission of an ejaculate. In this embodiment, the device 10 includes a ring, base, or cuff 20 that is removably positionable about a portion of a penis of an individual that desires to alter a sexual function such as delaying emissions. The device 10 also includes one or more a neuromodulation devices such as an ultrasound generator 30 attached to or incorporated as part of the cuff 20. In other example embodiments, other neuromodulation devices may be alternatively used or may be used in conjunction with or concomitantly with the ultrasound generator 30. Other neuromodulation devices including but not limited to electrical or mechanical stimulation may be used.

One of the purposes of the cuff 20 is to position the ultrasound generator or transducer 30 proximate a portion of a sexual organ, such as a penis, to be treated. The ultrasound generator or transducer 30 generates a wave of energy that stimulates or inhibits a nerve, such as the pudendal nerve or dorsal nerve of the penis, causing a change in sexual function (i.e., delay in an ejaculatory event). As will be discussed in more detail below, in one embodiment of the present invention, a controller 50 may be provided that can be used to control the ultrasound generator or transducer 30 or other features of the present invention.

As illustrated in FIG. 1, the ring or cuff 20 may extend about a circumference of a patient's penis. In one of the methods of treating or delaying sexual emissions, the ring or cuff 20 may be positioned generally close to a base of the penis, however, the ring or cuff 20 may be placed in any location on the sexual organ that may provide effective therapy. It should be noted that the location of effective therapy may be different for different individuals.

The ability to easily apply, move, or remove the device 10, is enhanced by the manufacture of the ring or cuff 20. In one example embodiment of the invention, the ring or cuff 20 may comprise a generally elastomeric material such that it can be stretched over the sexual organ prior to or during use. The cuff 20 may be manufactured from a durable yet supple material such as silicone. As the system 10 may be worn during intercourse, the cuff 20 should ideally have a profile that is either not noticed by a partner or enjoyable to the partner. Lastly, the material of the cuff 20 permits it to be easily cleaned after use. In other embodiments of the invention, the transducer housing 31 is detachable from the cuff 20. The transducer housing 31 may used with a variety of different cuffs having different styles. For example, the cuff 20 may have different thicknesses, protuberances, etc.

The ring or cuff 20 may also be adjustable to permit it to be adjusted to accommodate users of various sizes. The cuff 20 may be manufactured with various features that permit it to be adjustable. For instance, in one embodiment, the cuff 20 may comprise a hook and loop material wherein a user can adjust the cuff 20 size by manipulating a free end of the cuff and securing it to another portion of the cuff 20. In another embodiment, the cuff 20 may include a plurality of holes or apertures spaced along a portion of a free end of the cuff 20. The apertures may be releasably connectable to one or more of a plurality of posts or peg extending away from an outer surface of the cuff 20. In another example embodiment, the ring or cuff 20 may have a pair of opposed free ends that may be coupled together by a coupler 21. The coupler 21 may comprise a buckle, loop, clasp or any other similar device. Other adjustable mechanisms are also possible and the embodiments presented herein should not be considered limiting.

As illustrated in FIG. 2, the cuff 20 is used to support an ultrasound generator or transducer as well as power source. In various examples, transducer 30 includes a non-implantable transducer configured to generate an ultrasound output or wave 32 in response to a driving signal provided by controller 50 and conveyed to transducer 30 either wirelessly or by a connection 52. Ultrasound energy, in the form of mechanical vibrations, is then applied to the surface of the tissue of the penis by one or more energy emitting surface or probes 34. Energy emitting surface or probes 34 can be in direct physical contact with the tissue of the penis or sexual organ. In another embodiment, the energy emitting surface 34 can be positioned proximate the tissue of the penis or sexual organ.

The transducer 30 is configured to emit a wave at an ultrasound frequency in response to electrical energy. As particularly illustrated in FIG. 2, the emitted energy wave may be aligned generally normal with the emitting surface of the probes 34. However, in other example embodiments, transducer(s) 30 may have multiple emitting elements and may be generally aligned at varying angles. Although the invention has been illustrated showing a focused energy wave embodiments are also contemplated that has a transducer 30 that encircles the penis and emits energy waves circumferentially.

As illustrated in FIGS. 1 and 2, the transducer 30 may be positioned in a housing 31 made of a durable material such as polyvinyl chloride (PVC), polypropylene (PP), polyethylene (PE), polystyrene (PS) as well as nylon polyethylene terephthalate (PET), polyimide (PA), polycarbonate (PC), acrylonitrile butadiene (ABS), polyetheretherketone (PEEK) and polyurethane (PU) to name a few. The transducer 30 and its housing are ideally resistant to fluids and can be easily cleaned. The ring or cuff 30 may also be manufactured from a similar or dissimilar material as the housing 31. The housing 31 permits a user to remove the transducer 30 for the purpose of replacement or repair.

When the transducer 30 is activated it emits energy waves 32 toward a nerve, such as the dorsal nerve of the penis or pudendal nerve, that causes it to be stimulated or inhibited. As the energy waves travel transdermally through the penis or sexual organ, cavitation can occur that creates the formation of vapor cavities. These vapor cavities or small liquid-free zones ("bubbles" or "voids") are created by rapid changes of pressure. Where the pressure is low a void is created. When subjected to higher pressure, the voids implode and generate a shock wave. These shockwaves cause the dorsal nerve of the penis or pudendal nerve to be stimulated or inhibited.

The ultrasound generator or transducer 30 generally consists of a generator that responds to a high-frequency alternating current. The high frequency electric current is then converted by the transducer 30 into mechanical (acoustic) vibrations. The transducer 30 consists of a crystal inserted between two electrodes. As an alternating electrical charge is applied to the surfaces of the crystal, the crystal is made to vibrate rapidly creating sound waves.

In still yet another embodiment of the invention, the transducer(s) 30 can generate an energy wave or vibration through a coupling medium. It is known that ultrasound waves are transmitted more effectively through water, oil, or transmission gel than through air. Consequently, as illustrated in FIG. 3, a coupling member 36 may be used to "couple" the emitting surface 34 of the transducer 30 to the patient's penis in order to ensure that the ultrasound waves are properly transmitted to the desired treatment site. The coupling member 36 may, for example, be in the form of a gel or lotion which is applied to the skin of the patient over the area to be treated. The transducer 30 may then be positioned on the coupling member 36, and the generator is activated. Ultrasound waves 32 produced at the emitting surface 34 are transmitted through the coupling member 36 into the patient to stimulate the dorsal nerve of the penis or pudendal nerve.

In another example embodiment of the invention, the coupling member 36 may comprise a sheet, pad, or disk of material that is capable of transferring sound waves into the penis of the patient. The coupling member 36 may have generally opposed planar surfaces 37A, 37B that permit the planar surfaces to be placed against the skin of the patient's penis and the emitting surface 34 of the transducer 30. The planar surfaces 37A, 37B may be covered by a film member 38A, 38B that permit the surfaces of the coupling member 36 to remain free of debris. In embodiments where the coupling member 36 comprises a solid or semi solid material, such as a gel, the films 38A, 38B permit the coupling member 36 to retain its moisture content. These pads of coupling member 36 can be sold together with the transducer or sold separately to permit a user to reuse the system device or system 10.

The properties of the transducer 30 depend upon its diameter and frequency. For example, a small diameter produces a generally small diameter ultrasound beam. In an example embodiment of the invention, ultrasound frequencies of about 400 khz may be used to stimulate the dorsal nerve of the penis or pudendal nerve. A range of ultrasound frequency to include 0.5 to 3 MHz may also be used to treat the nerve. A practitioner may use the controller 50 to select a particular frequency depending upon the dimension of the patient.

In an example embodiment of the invention, the other parameters of the system 10 may comprise:
- a pulse width of 1 msec, and a treatable range of 0.01 to 5,000 msec
- a stimulation frequency of 100 Hz
- an ultrasound treatable range of 0.5 to 3 MHz or 0.5 to 5 MHz
- an acoustic power in a treatable range of 400 $W/cm^2$ to 7,500 $W/cm^2$ Other treatable ranges are possible and may be used to treat various conditions. Therefore, the above cited ranges should not be considered limiting.

In yet another example embodiment, the ultrasound waves 32 may create heat or cooling thermal stresses, for instance by the process of cavitation discussed herein, that are focused in the general area of the dorsal nerve of the penis or pudendal nerve. The focused heat or cooling of the ultrasound wave can cause localized thermal stress that stimulates or inhibits the dorsal or pudendal nerve. In yet another example embodiment, the transducer 30 may include a heating or cooling element that is capable of generating heat or cold to stimulate or inhibit the dorsal nerve of the penis or pudendal nerve. A user may select the heating or cooling element, the transducer 30 or both to stimulate or inhibit the dorsal nerve of the penis or pudendal nerve. In other example embodiments, the nerve may be stimulated by electrical, chemical, magnetic or mechanical elements that can be built into the housing of the transducer 30. Elements distinct from the transducer 30 are also contemplated.

To activate the transducer 30 or other elements within the ring or cuff 20, a wired or wireless activation device or controller 50 may be used. The controller 50 can be controlled by the person being treated or their partner. The controller 50 permits a partner to alter the sexual function, such as delaying ejaculation, until a desired period of time. This ensures that both parties are able to achieve the sexual satisfaction that they desire.

The controller 50 may comprise a smart phone. However, any other type of control device may be used, including but not limited to wireless smart watches. The system 10 may also use a controller 50 that is dedicated to the transducer 30. This dedicated device may be wired or wireless. Independent of the type of controller 50 utilized, it should have the functionality to control (i.e., turn on and off the transducer 30 and other elements) the device or system 10. It may also be able to vary the frequency of the generated sound waves 32. Other control features are also contemplated herein and the above should not be considered limiting.

The ring or cuff 20 or housing 31 of the transducer 30 may also house one or more sensors that can sense the frequency of the sound waves 32, the physiological state of the penis (e.g., using penile contractions to determine an ejaculatory event), or other conditions such as heat, cold, time, etc. The controller 50 may also be used to control the sensitivity of the transducer 30 or elements to further change a sexual function such as delaying the onset of ejaculate emissions. The controller 50 is designed so that it may be held or worn on various parts of the body and activated by voice or other mechanisms.

Figure 5:
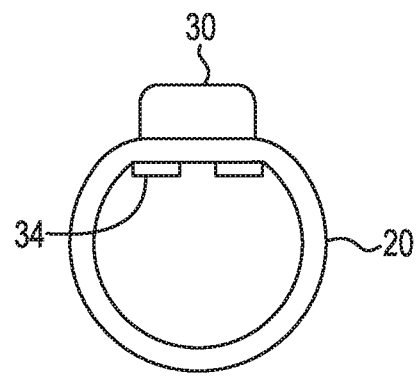
FIG. 5 is an end view of a premature ejaculation treatment system with an elastic ring or base according to an example embodiment of the invention.
Figure 6:
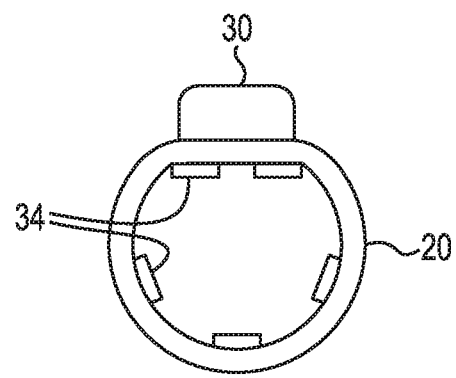
FIG. 6 is an end view of a premature ejaculation treatment system with an array of transducers according to an example embodiment of the invention.
Figure 7:
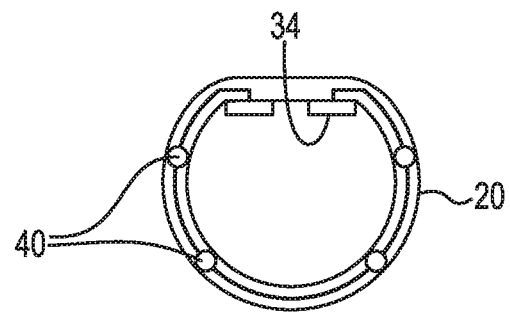
FIG. 7 is a cross sectional view of a premature ejaculation treatment system with one or more power supplies embedded with in a ring according to an example embodiment of the invention.

As illustrated in FIGS. 5-7, the ring or cuff 20 may incorporate the transducer 30, probes 34, other elements (such as power supplies 40) and sensors into its construction so that its profile is minimized. As particularly illustrated in FIG. 5, the probes 34 are positioned proximate the transducer 30. In this embodiment, a user uses the position of the housing 31, and thus the probes 34, to correctly position the device or system 10 at a particular therapy location.

In another embodiment of the invention, as illustrated in FIG. 6, the ring or cuff 20 may include a plurality of probes 34 positioned about the cuff 20. The probes 34 are operatively coupled to the transducer 30 to emit energy about the circumference of the cuff 20. In this particular embodiment, the probes 34 may be spaced apart or may be positioned proximate to each other to affect a continuous energy wave around a circumference of the cuff 20.

As illustrated in FIG. 7, one or more power supplies 40 may be positioned in the ring or cuff 20 to power the transducer probes 34. The power supplies 40 and transducer probes 34 may be operatively coupled by an elastic, flexible and/or stretchable conductive material that permits continuous operation of the device or system 10 during adjustment of the cuff 20. In this particular embodiment, the housing 31 may be eliminated and the transducer 30 incorporated into the cuff 20. The design of this embodiment provides a more slim profile that may be advantageous for use during a sexual event or encounter. It should be understood that this design may be incorporated into any of the aforementioned embodiments.

Figure 8:
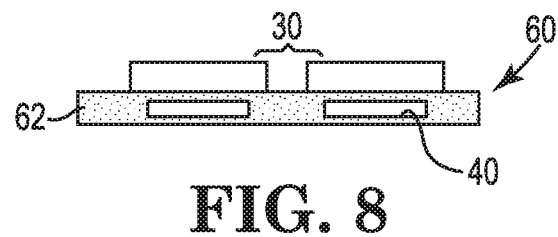
FIG. 8 is an end view of a disposable or reusable premature ejaculation treatment patch with one or more power supplies and transducers according to an example embodiment of the invention.

As illustrated in FIG. 8, in an example embodiment of the invention, the system 10 may comprise a removable patch 60 that may be worn by a user to treat a sexual dysfunction such as unintended sexual emissions or climax. The patch 60 comprises a base member 62 that can house one or more power supplies 40. The power supplies 40 are operatively coupled to one or more transducers 30 that can be positioned and removably adhered against a user's tissue to be treated. As discussed above, the transducer(s) 30 may have a transmitting medium 36 positioned thereon that aids in transmission of the energy waves to the user's therapy location.

The patch 60 can include an actuating mechanism that uses the conductive nature of a user's skin to complete a circuit. For instance, once the device 10 is placed on the user the circuit is completed and the device 10 is activated. When it is activated the transducer(s) 30 generates energy waves for therapeutic purposes. Once the device 10 is removed the circuit is broken and the transducer 30 stops producing energy waves. Other actuating control mechanisms are also contemplated herein and may include the controller 50 discussed above.

Figure 9:
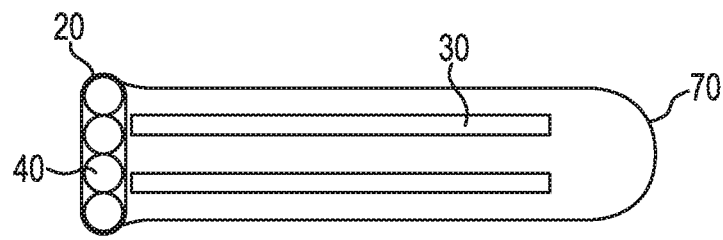
FIG. 9 is a side view of a premature ejaculation treatment system having a sleeve according to an example embodiment of the invention.
Figure 10:
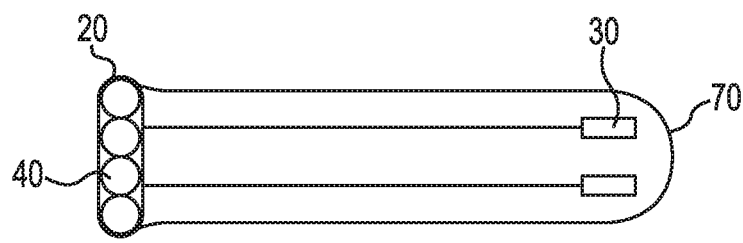
FIG. 10 is a side view of a premature ejaculation treatment system having a sleeve according to an example embodiment of the invention.

As illustrated in FIGS. 9 and 10, another embodiment of the present invention incorporates sexual dysfunction treatment with sexually transmitted disease ("STD") prevention. In these particular embodiments, the device or system 10 includes a sheath 70 incorporated with a ring or cuff 20. The sheath 70 includes one or more transducers 30 that are located in a therapeutic location when worn by a user. The transducer(s) 30 may be located along a length or circumference of the sheath 70 (as illustrated in FIG. 9) or may be located in a particular location, such as the tip (as illustrated in FIG. 10) or base of the organ. The transducer(s) 30 may be operatively coupled to one or more power supplies 40 incorporated in the cuff 20. The embodiments of FIGS. 9 and 10 may be worn during a sexual event and then discarded. In another example embodiment, the sheath 70 may be cleaned and reused and the power supplies 40 may be recharged.

As discussed throughout, the cuff 20, patch 60 or sheath 70 may be worn during intercourse. It is also possible however, that each may be worn during a non-sexual encounter treatment period. For instance, the cuff 20, patch 60 or sheath 70 may be worn under clothing, which permits a user to activate a treatment session at any time and at any location. One of the advantages of the present invention is that it is discrete and can be used to deliver therapy prior to a sexual encounter.

Figure 11:
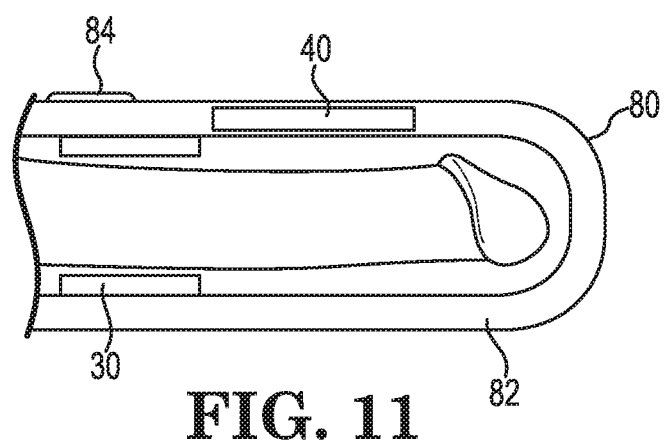
FIG. 11 is a cross sectional view of a premature ejaculation treatment system in use according to an example embodiment of the invention.

As illustrated in FIG. 11, the system 10 of the present invention also includes a reusable therapy sleeve 80 that can be used to administer therapy. The sleeve 80 may be a generally rigid or flexible tube that has a closed end and an open end that is adapted to receive a penis of a user. The sleeve 80 includes side walls 82 that are able to support one or more transducers 30 that are positioned to provide therapy to a user's penis. The transducer(s) 30 may be mounted to an inner surface of the sleeve 80 or may be embedded therein. The sleeve 80 may also include probes 34 so as to position the transducer(s) 30 a distance from the treatment location.

The side wall 82 of the sleeve 80 is also designed to support one or more power supplies 40 that are operatively coupled to the transducer(s) 30. The power supplies 40 may be wirelessly recharged. The sleeve 80 may also include a power cord that allows a user to plug in the sleeve 80 to recharge the power supplies 40.

In one example embodiment of the invention, the sleeve 80 may include an actuator 84 to allow a user to control the power flowing to the transducer(s) 30. The actuator 84 may comprise a switch mounted on the sleeve 80 or may comprise a wireless or wired controller 50. As discussed above, the controller 50 may comprise a smart device such as a phone or watch.

In still another embodiment of the invention, the system 10 may be implantable into a patient. The implantable device or system includes a biocompatible housing, internal therapy circuitry such as an ultrasound producing or electrical producing system. Leads may be implanted and disposed proximate a nerve, such as the dorsal nerve of the penis or pudendal nerve, that is capable of treating premature ejaculation.

The implantable system may be implanted in an office setting by using a delivery system that includes a delivery needle that may be inserted into the pubis region of patient. In one example embodiment, the delivery needle may be inserted into a patient's uretha to deliver the system 10 into the patient's pubis. In yet another example embodiment, the delivery needle may be inserted transabdominally to deliver the system into the pubis region of the patient. The system 10 may be positioned in an anterior portion of the pubis or the base of the penis such that it is positioned proximate the dorsal nerve of the penis or pudendal nerve. Ideally the system 10 is positioned proximate the dorsal nerve of the penis or pudendal nerve and may be activated transdermally by the controller 50. In the implantable embodiment, the transducer 30 includes a rechargeable power supply that can be recharged transdermally. One of the advantages of the implantable embodiment is that a user's partner is unaware of the use of the system 10.

In use, a user or physician locates the dorsal nerve of the penis or pudendal nerves of the penis 60. The user or their partner then positions the cuff 20, patch 60, sheath 70 or sleeve 80 on the penis and positions it so that the transducer(s) 30 is proximate the nerve 62 to be treated. In some embodiments, the user or their partner may then remove the film 38A, 38B from the coupling member 36 and position the coupling member 36 between the emitting surface 34 of the transducer(s) 30 and the penis. In step 64 of FIG. 4, the user or their partner may then use the controller 50 or actuator 84 to activate the transducer(s) 30. The transducer(s) 30 then emits sound waves 34, as seen in step 66 of FIG. 4. If the system 10 is being used during intercourse the user and their partner can begin to have intercourse 68. Once either the user or partner wants to permit the treated user to ejaculate, the user or the partner may use the controller 50 to switch off the transducer(s) 30, thereby ceasing the sounds wave 34 and permitting the user to ejaculate 70.

In one embodiment of the invention, the device 10 is capable of increasing or decreasing the intensity of the therapy over a particular period of time. For instance, the device 10 is able to apply an amount of therapy, for example sound energy, which is not perceptible to a patient or user. The device 10 is then able to incrementally increase the intensity of the therapy to a pre-set level. After a certain period of time, the device 10 is able to incrementally decrease the intensity of the therapy. The therapy is capable of cycling the therapy levels for a period of time. In another example embodiment of the invention, a user or third party is able to manual adjust the intensity level and/or duration of the therapy session.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A device for altering a sexual emission of a penis, the device comprising:
  a cuff adapted to be fit about at least a portion of the penis;
  an energy generator operatively disposed to the cuff, the energy generator being adapted to generate and deliver continuous energy to the penis capable of disrupting a nerve of the penis;
  at least one sensor configured to sense an approaching sexual emission and automatically adjusting the energy being delivered to the penis; and
  wherein a sexual emission of the penis is delayed.

2. The device of claim 1, further comprising a power supply operatively coupled to the energy generator to provide power thereto.

3. The device of claim 1, wherein the cuff includes a housing adapted to removably receive the energy generator or power supply.

4. The device of claim 1 further comprising a controller adapted to control the energy generator.

5. The device of claim 1, further comprising a sheath extending away from the cuff, the sheath being adapted to cover a penis.

6. The device of claim 5, further comprising one or more energy generators being disposed on the sheath and adapted to deliver therapy to the penis.

7. A therapy system for altering a sexual emission of a penis, the system comprising:
  an energy generator positionable on at least a portion of the penis, the energy generator adapted to generate and deliver continuous energy to the penis energy capable of disrupting nerves of the penis;
  at least one sensor configured to sense an approaching sexual emission and automatically adjusting the energy being delivered to the penis; and
  wherein the disruption of the nerves delays an ejaculatory event.

8. The therapy system of claim 7, wherein the energy generator comprises a sleeve having an open end and a peripheral wall extending therefrom, the open end being capable of receiving the penis to be treated, the sleeve having one or more energy generators disposed on its peripheral wall to position the energy waves proximate a therapy location on the penis.

9. The therapy system of claim 7, wherein the energy generator comprises an elastic cuff removably fit about at least a portion of the penis, the elastic cuff having one or more energy generators disposed thereon to position the energy waves proximate a therapy location on the penis.

10. The therapy system of claim 9, further comprising a sheath extending away from the elastic cuff, the sheath being adapted to cover at least a portion of the penis to be treated.

11. The therapy system of claim 10, further comprising one or more transducers disposed on the sheath to position the energy waves proximate a therapy location on the penis.

12. A method of treating sexual dysfunction of a penis, the method comprising the steps of:
    placing an energy-generator capable of generating energy on a portion of the penis to be treated;
    activating the generator to generate and deliver continuous energy to the penis that disrupt a nerve of the penis being treated;
    at least one sensor being provided that is configured to sense an approaching sexual emission and automatically adjusting the energy being delivered to the penis; and
    wherein the ejaculatory event is delayed.

13. The method of claim 12 further comprising the step of engaging in sexual intercourse while the energy-generator is generating energy.

14. The method of claim 12 further comprising the step of treating the penis with energy prior to engaging in sexual intercourse.

15. The method of claim 12, further comprising the step of using a remote controller operatively coupled to the energy generator to control the generating of energy.

16. The method of claim 13 further comprising the step of stopping the generation of energy to cease nerve disruption and to permit an ejaculatory event.

17. The method of claim 13 further comprising the step of permitting a sexual partner to control the cessation of energy to permit a user being treated to experience an ejaculatory event.

18. The method of claim 17 further comprising a remote control operatively coupled to the energy generator and operatable by the sexual partner to remotely control cessation of the energy.

19. The method of claim 12 further comprising the step of using the at least one sensor to detect a penile contraction as an approaching ejaculatory event, the at least one sensor being positionable about the penis.

20. The method of claim 19 further comprising the step of adjusting the energy generator to increase or decrease the energy for the purpose of disrupting the nerves of the penis and delaying the ejaculatory event.

* * * * *